United States Patent [19]
Mizunashi et al.

[11] Patent Number: 5,705,386
[45] Date of Patent: Jan. 6, 1998

[54] CIRCULAR PLASMIDS

[75] Inventors: Wataru Mizunashi; Fujio Yu, both of Kanagawa, Japan

[73] Assignee: Nitto Chemical Industry Co. Ltd., Tokyo, Japan

[21] Appl. No.: 678,650

[22] Filed: Jul. 11, 1996

[30] Foreign Application Priority Data

Jul. 20, 1995 [JP] Japan .................................. 7-205062

[51] Int. Cl.⁶ .................................................. C12N 15/63
[52] U.S. Cl. ........................................................ 435/320.1
[58] Field of Search ........................... 435/320.1; 935/22, 935/23, 27, 29

[56] References Cited

U.S. PATENT DOCUMENTS 5,246,857  9/1993  Yu et al. ............................... 435/320.1

FOREIGN PATENT DOCUMENTS 0502476  9/1992  European Pat. Off. ........ C12N 15/74

*Primary Examiner*—James Ketter
*Assistant Examiner*—Irem Yucel
*Attorney, Agent, or Firm*—Steinberg, Raskin & Davidson P.C.

[57] ABSTRACT

The specification relates to circular plasmids derived from microorganisms of the genus Rhodococcus, which have sizes of about 3.6 kb and restriction site numbers of BamHI:1, BglII:1, ClaI:1, PstI:1, PvuII:2 and SacI:1. The circular plasmids of the present invention are useful as vectors in industrially useful host-vector systems.

3 Claims, 1 Drawing Sheet

CIRCULAR PLASMIDS

BACKGROUND OF THE INVENTION

The present invention relates to novel plasmids, more specifically to novel plasmids derived from microorganisms of the genus Rhodococcus.

It is known that microorganisms of the genus Rhodococcus are industrially very useful because they can produce a wide variety of useful substances such as enzymes participating in the metabolism of nitriles, enzymes participating in the decomposition of PCB (polychlorobiphenyl) and the like, and biosurfactants which can be used in the treatment of waste water.

However, the development of vectors which are suitable for use in host microorganisms of the genus Rhodococcus has not made much progress. Plasmids were found in only a few strains of Rhodococcus such as Rhodococcus sp. H13-A (J. Bacteriol. 170, 638–645 (1988)), and Rhodococcus rhodochrous ATCC 4276, ATCC 14349, ATCC 14348, ATCC 4001, etc. which were found by the inventors (see U.S. Pat. No. 5,246,857 (Japanese Unexamined Patent Publication Nos. Hei 4-148685 and 4-330287)).

Particularly in the case where these host-vector systems are to be used industrially, they are believe to be desirably used in self-cloning systems in order to insure safety of recombinant DNA-containing microorganisms. However, the problem is that only *Rhodococcus rhodochrous* can be at present used for self-cloning systems. Hence, there has been a strong need to develop new vectors that can be used to create industrially useful microorganisms.

SUMMARY OF THE INVENTION

As a result of the various studies conducted to develop industrially useful host-vector systems by using microorganisms of the genus Rhodococcus, the inventors found a novel circular plasmid from a microorganism of the genus Rhodococcus which can be used as a vector in industrially useful host-vector systems. The present invention was accomplished on the basis of this finding. Thus, in accordance with the present invention, circular plasmids are provided that are derived from microorganisms of the genus Rhodococcus, that have sizes of about 3.6 kb and that are characterized by the following restriction site numbers, BamHI:1, BglII:1, ClaI:1, PstI:1, PvuII:2 and SacI:1. The circular plasmids of the present invention are useful as vectors in industrially useful host-vector systems.

DESCRIPTION OF THE PREFERRED EMBODIMENT

Figure 1:
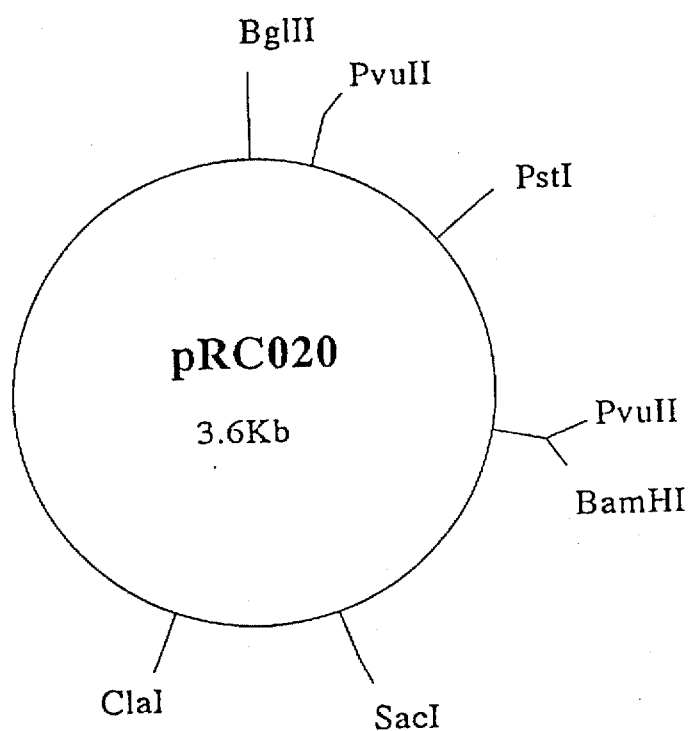
FIG. 1 is a restriction map of plasmid pRC020.

In accordance with an embodiment of the present invention, the plasmid can be obtained from, for example, *Rhodococcus erythropolis* ATCC 21035. This plasmid is a novel circular plasmid which has a size of about 3.6 kb and the characteristics of cleavage with restriction enzymes as shown in Table 1. This plasmid will be hereinafter referred to as "pRC020".

TABLE 1

| Restriction Enzyme | The Number of Cleavage Sites | Sizes of Created Fragments (kb) |
|---|---|---|
| BamHI | 1 | 3.6 |
| BglII | 1 | 3.6 |
| ClaI | 1 | 3.6 |
| PstI | 1 | 3.6 |
| PvuII | 2 | 2.75, 0.85 |
| SacI | 1 | 3.6 |

The following example is submitted to illustrate but not to limit the present invention.

EXAMPLE 1

Isolation and Purification of Plasmid

*Rhodococcus erythropolis* ATCC 21035 was inoculated into 100 ml of an MY medium (0.5% polypeptone, 0.3% bactoyeast extract, 0.3% malt extract, 1% glucose). After 24 hours of cultivation, a 20% sterilized glycine solution was added to the culture at a final concentration of 2% and the cultivation was performed for additional 24 hours. The cells were then collected by centrifugation. The collected cells were washed with 40 ml of a TES buffer (10 mM Tris-HCl (pH 8), 10 mM NaCl, 1 mM EDTA) and suspended in 11 ml of a lysozyme solution (50 mM Tris-HCl (pH 8), 12.5% sucrose, 100 mM NaCl and 1 mg/ml lysozyme), followed by shaking of the mixture at 37° C. for 3 hours. To the culture, 1 ml of 10% SDS was added and the mixture was shaken gently for 1 hour. Further, 1 ml of a 3M sodium acetate buffer (pH 5.2) was added to the culture and the mixture was left to stand on ice for 1 hour. The culture was then centrifuged at 4° C. at 10,000× g for 1 hour. To the supernatant, five volumes of ethanol were added and the mixture was left to stand at −20° C. for 30 minutes, followed by centrifugation at 10,000× g for 20 minutes. The precipitate was washed with 30 ml of 70% ethanol and then dissolved in 1 ml of a TE buffer to give a plasmid fraction.

The plasmid fraction was subjected to 0.7% agarose gel electrophoresis. The gel was stained with ethidium bromide to confirm the presence of the plasmid.

Determination of Molecular Weight of Plasmid

Part of the plasmid thus prepared was subjected to 0.7% agarose gel electrophoresis. In the electrophoresis, *E. coli* plasmids pUC18 (size: 2.69 kb), pUC118 (size: 3.16 kb), pTrc99A (size: 4.17 kb) were electrophoresed as size markers at the same time. The plasmid obtained from *Rhodococcus erythropolis* ATCC 21035 was designated as "pRC020". The size of pRC020 was about 3.6 kb as determined by agarose gel electrophoresis.

Cleavage Specificity for Various Restriction Enzymes

Part of the plasmid thus prepared was reacted with various restriction enzymes. After the reaction, the reaction solution was analyzed by 0.7% agarose gel electrophoresis and 5% acrylamide gel electrophoresis. The HindIII and PstI digestion products of lambda phage DNA were used as size markers to calculate the sizes of various restriction fragments of the plasmid. The characteristics of pRC020 for cleavage with various restriction enzymes are shown in Table 2.

TABLE 2

| Restriction Enzyme | The Number of Cleavage Sites | Sizes of Created Fragments (kb) |
|---|---|---|
| BamHI | 1 | 3.6 |
| BglII | 1 | 3.6 |
| ClaI | 1 | 3.6 |
| EcoRI | 0 | — |
| HindIII | 0 | — |
| PstI | 1 | 3.6 |
| PvuII | 2 | 2.75, 0.85 |
| SacI | 1 | 3.6 |
| ScaI | 0 | — |
| SmaI | 0 | — |
| SphI | 0 | — |
| SplI | 0 | — |
| XhoI | 0 | — |

What is claimed is:

1. An isolated circular plasmid obtained from a microorganism of the genus Rhodococcus; which has a size of about 3.5 kb, wherein the restriction sites have the following order: BglII, PvuII, PstI, PvuII, BamHI, SacI and ClaI.

2. The isolated circular plasmid of claim 1, wherein the microorganism is *Rhodococcus erythropolis* ATCC 21035.

3. The isolated circular plasmid of claim 2, wherein said plasmid is pRC020.

* * * * *

UNITED STATES PATENT AND TRADEMARK OFFICE
CERTIFICATE OF CORRECTION

PATENT NO. : 5,705,386
DATED : January 6, 1998
INVENTOR(S) : Mizunashi, et al.

It is certified that error appears in the above-identified patent and that said Letters Patent is hereby corrected as shown below:

At column 1, line 63, after *Rhodococcus erythropolis* delete "ATCC 21035" and insert --FERM BP-6112. A deposit of this strain was made on September 18, 1997 with the National Institute of Bioscience and Human-Technology, Agency of Industrial Science and Technology, 1-3, Higashi 1-chome, Tsukuba-shi, Ibaraki-ken, 305 Japan under the accession number FERM BP-6112.--

At column 2, line 19, and column 2, lines 51-52, after *Rhodococcus erythropolis* delete "ATCC 21035" and insert --FERM BP-6112--.

At column 4, line 9, after *Rhodococcus erythropolis* delete "ATCC 21035" and insert --FERM BP-6112--.

Signed and Sealed this

Twenty-eighth Day of April, 1998

*Attest:*

BRUCE LEHMAN

*Attesting Officer*   Commissioner of Patents and Trademarks